(12) United States Patent
Yuds et al.

(10) Patent No.: US 12,171,924 B2
(45) Date of Patent: Dec. 24, 2024

(54) MOBILE CART AND DOCKING STATION FOR USE WITH A MEDICAL DEVICE

(71) Applicants: Fresenius Medical Care Holdings, Inc., Waltham, MA (US); Fresenius Medical Care Deutschland GmbH, Bad Homburg (DE)

(72) Inventors: David Yuds, Hudson, NH (US); Jessica Steuber, Ashland, MA (US); Jonathan Leclerc, Northborough, MA (US); Johanness Thoelking, Mannheim (DE)

(73) Assignees: Fresenius Medical Care Holdings, Inc., Waltham, MA (US); Fresenius Medical Care Deutschland GmbH, Bad Homburg (DE)

( * ) Notice: Subject to any disclaimer, the term of this patent is extended or adjusted under 35 U.S.C. 154(b) by 1031 days.

(21) Appl. No.: 17/136,758

(22) Filed: Dec. 29, 2020

(65) Prior Publication Data
US 2022/0203007 A1 Jun. 30, 2022

(51) Int. Cl.
*A61M 1/28* (2006.01)
*A61L 2/10* (2006.01)
(Continued)

(52) U.S. Cl.
CPC .............. *A61M 1/282* (2014.02); *A61L 2/10* (2013.01); *A61L 2/26* (2013.01); *B60L 53/30* (2019.02);
(Continued)

(58) Field of Classification Search
CPC .................. A61M 1/281; A61M 1/282; A61M 2205/3576; A61M 2205/8243;
(Continued)

(56) References Cited

U.S. PATENT DOCUMENTS 9,186,449 B2 * 11/2015 Singh .................... A61M 1/288
10,086,124 B2 10/2018 Singh et al.
(Continued)

FOREIGN PATENT DOCUMENTS

CN 112023161 A 12/2020

OTHER PUBLICATIONS

International Patent Application No. PCT/US2021/063414, Partial Search Report (Mar. 22, 2022).

*Primary Examiner* — Edward Tso
*Assistant Examiner* — Aaron Piggush
(74) *Attorney, Agent, or Firm* — Leydig, Voit & Mayer, Ltd.

(57) ABSTRACT

A mobile cart for a medical device is disclosed. The cart is designed to transport a medical device such as a dialysis machine (e.g., a peritoneal dialysis (PD) machine). The medical device can be connected to a power supply included in the cart, where the power supply includes one or more energy storage devices (e.g., batteries), a charging circuit, and (optionally) an inverter. The cart can also include a number of features such as automatic brakes, UV light sterilization, sensors such as object detection safety features, environmental sensors, and the like. The cart can include electronic components that enables certain functionality such as hosting a wireless local area network or communicating wirelessly with the medical device. A docking station is also disclosed that enables wireless charging of the power supply such that neither the medical device nor the cart needs to be plugged into an external power supply.

16 Claims, 9 Drawing Sheets

(51) Int. Cl.
*A61L 2/26* (2006.01)
*B60L 53/30* (2019.01)
*B62B 3/02* (2006.01)
*B62B 5/04* (2006.01)

(52) U.S. Cl.
CPC .............. *B62B 3/02* (2013.01); *B62B 5/0404* (2013.01); *A61L 2202/11* (2013.01); *A61L 2202/16* (2013.01); *A61M 1/281* (2014.02); *A61M 2205/3576* (2013.01); *A61M 2205/8243* (2013.01); *A61M 2209/086* (2013.01)

(58) Field of Classification Search
CPC ...... A61M 2209/086; A61L 2/10; A61L 2/26; A61L 2202/11; A61L 2202/16; B60L 53/30; B62B 3/02; B62B 5/0404; B62B 5/0433
USPC .............................. 320/107, 108, 109; 604/28
See application file for complete search history.

(56) References Cited

U.S. PATENT DOCUMENTS

| | | | |
|---|---|---|---|
| 2016/0211695 A1* | 7/2016 | Singer | H02J 7/0042 |
| 2017/0141601 A1 | 5/2017 | Halliburton et al. | |
| 2018/0132966 A1* | 5/2018 | Desaulniers | A61L 2/10 |
| 2019/0381229 A1* | 12/2019 | Biewer | A61M 1/28 |
| 2020/0188543 A1* | 6/2020 | Etter | A61L 2/26 |

\* cited by examiner

MOBILE CART AND DOCKING STATION FOR USE WITH A MEDICAL DEVICE

BACKGROUND

Dialysis is a treatment used to support a patient with insufficient renal function. The two principal treatment options are hemodialysis (HD) and peritoneal dialysis (PD). During hemodialysis, the patient's blood is removed, e.g., via an arteriovenous (AV) fistula or other methods (e.g., AV graft), and passed through a dialyzer of a dialysis machine while also passing a dialysis solution, referred to as dialysate, through the dialyzer. A semi-permeable membrane in the dialyzer separates the blood from the dialysate within the dialyzer and facilitates the exchange of waste products (e.g., urea, creatine, potassium, etc.) between the blood stream and the dialysate. The membrane prevents the transfer of blood cells, protein, and other important components in the blood stream from entering the dialysate solution. The cleaned blood stream is then returned to the patient's body. In this way, the dialysis machine functions as an artificial kidney for cleaning the blood in patients with insufficient renal function.

In contrast with hemodialysis, the peritoneal dialysis treatment option introduces dialysate into a patient's peritoneal cavity, which is an area in the abdomen between the parietal peritoneum and visceral peritoneum (e.g., a space between the membrane that surrounds the abdominal wall and the membranes that surround the internal organs in the abdomen). The lining of the patient's peritoneum functions as a semi-permeable membrane that facilitates the exchange of waste product between the bloodstream and the dialysate, similar in function to the membrane in the dialyzer of the hemodialysis machine. The patient's peritoneal cavity is drained and filled with new dialysate over a number of PD cycles. Peritoneal dialysis can be performed using either gravity or an automated pumping mechanism to fill and drain the abdomen during a PD cycle.

Automated PD machines, sometimes referred to as PD cyclers, are designed to control the PD treatment process so that it can be performed at home without clinical staff, typically while the patient sleeps overnight so as to minimize interference with the patient's life. The process is referred to as continuous cycler-assisted peritoneal dialysis (CCPD). Many PD cyclers are designed to automatically infuse, dwell, and drain dialysate to and from the peritoneal cavity. The PD treatment typically lasts several hours, often beginning with an initial drain phase to empty the peritoneal cavity of used or spent dialysate that was left in the peritoneal cavity at the end of the last PD treatment. The sequence then proceeds through a progression of fill, dwell, and drain phases that follow sequentially. A group of fill, dwell, and drain phases, in order, can be referred to as a PD cycle.

Typically, an automated PD machine is placed near a chair or bed so that the patient can remain comfortable while being relatively immobile during the treatment cycle. The patient may be attached to the PD machine by tubing that can range from a few feet in length to around 10 feet, which allows the user to get up and move around the room if needed. However, it is difficult to move between rooms without pausing the treatment and physically relocating the PD machine.

Moving a PD machine from one room to another can involve disconnecting the PD machine from a power source, such as a wall outlet, disconnecting one or more dialysate bags connected to the PD machine, moving the PD machine to another location, and reconnecting the dialysate bags and power in the new location. The PD machine itself can be relatively cumbersome, as they can be both large and heavy. Thus, most patients that desire mobility choose another method for their PD treatment. One solution is to perform the treatment manually (i.e., without an automated PD machine), which is referred to as Continuous Ambulatory Peritoneal Dialysis (CAPD), by raising a connected bag of dialysate solution above the abdomen during a fill phase and later placing a drain below the abdomen during a drain phase. However, this method of treatment can be tedious and is not as precise as treatment controlled by an automated PD machine.

Some PD machines include internal back-up battery supplies to prevent failures during short-term power faults with the electrical supply. These battery backups can allow for continued treatment for a short period of time while a user moves the PD machine to a new location and plugs the PD machine into an electrical outlet in the new location. However, the time allowed to move the PD machine is limited by the battery capacity, and adding additional batteries increases the weight of the PD machine, making it more difficult to move. Further, requiring a patient to carry a heavy machine, bend over to unplug or plug the PD machine back into the electrical outlet, and the like, can increase a patient's blood pressure or have other undesirable medical consequences. Thus, there is a desire to create a mobile solution that enables patients to more easily move a PD machine during treatment.

SUMMARY

In accordance with one aspect of the disclosure, a cart is provided that includes a number of features that allow a medical device to operate while the medical device is moved between locations. The cart includes a power supply that is sufficient to power the cart for a duration of a treatment session. The cart may also be charged via wireless inductive charging such that the cart never needs to be tethered to a wall outlet to recharge the power supply.

In accordance with a first aspect of the disclosure, a system for use with a medical device is disclosed. The system includes a cart and a docking station. The cart includes a power supply including one or more energy storage devices and a charging circuit. The docking station is connected to an electrical supply and configured to provide power to the charging circuit to recharge the one or more energy storage devices when the cart is proximate the docking station. The medical device can be disposed on the cart and connected to the power supply to provide power to the medical device while the cart is in motion.

In some embodiments, the docking station includes a primary coil and the charging circuit includes a secondary coil. The primary coil induces a current in the secondary coil when the cart is proximate the docking station. This operation can be referred to as inductive charging.

In some embodiments, a switch or sensor activates the primary coil when the cart is detected proximate the docking station.

In some embodiments, the cart also includes a plurality of casters; an automatic braking system; and one or more sensors for detecting objects in a path of the cart while the cart is in motion. Responsive to detecting an object in the path of the cart, a controller engages the automatic braking system to stop the motion of the cart.

In some embodiments, the cart also includes one or more lights, and at least one of the lights includes an ultraviolet (UV) light source for sterilizing at least one surface proximate the cart. In an embodiment, the cart also includes an extendable tray that can be stowed under a top surface of the cart. A UV light of the one or more lights is attached to an underside of the top surface such that the extendable tray is at least partially sterilized when in a stowed position.

In some embodiments, the medical device is a peritoneal dialysis (PD) machine, and the cart also includes a peritoneal dialysis assistance device. In one embodiment, the peritoneal dialysis assistance device comprises a line management system.

In some embodiments, the cart also includes a communications module configured to: provide a wireless access point (AP) for one or more accessories associated with the cart; or stablish a wireless communication channel with the medical device.

In accordance with a second aspect of the present disclosure, a system for performing peritoneal dialysis (PD) is disclosed. The system includes a cart and a PD machine disposed on the cart. The cart comprises a power supply including one or more energy storage devices and a charging circuit.

In some embodiments, the system also includes one or more docking stations that, when the cart is disposed proximate any of the one or more docking stations, provide power to the charging circuit via wireless inductive charging.

In some embodiments, the cart also includes a communications module for establishing a wireless communications channel with the PD machine.

In an embodiment, the PD machine is configured to: initiate a dialysis treatment cycle that includes at least one of a drain phase, a fill phase, or a dwell phase; receive a signal from the cart via the wireless communications channel indicating the cart is in motion; responsive to receiving the signal indicating that the cart is in motion, pause the dialysis treatment cycle; receive a signal from the cart via the wireless communications channel indicating the cart is stationary; and responsive to receiving the signal indicating that the cart is stationary, resume the dialysis treatment cycle. In an embodiment, pausing the dialysis treatment cycle comprises at least one of: clamping at least one line connected to the PD machine; or moving at least one pump to a home position.

In some embodiments, the cart also includes: a plurality of casters; an automatic braking system; and one or more sensors for detecting objects in a path of the cart while the cart is in motion. Responsive to detecting an object in the path of the cart, a controller engages the automatic braking system to stop the motion of the cart.

In some embodiments, the cart also includes a tablet computer including a display. The tablet computer is connected to a network to enable a patient to participate in a video conference with a health professional.

In accordance with a third aspect of the present disclosure, a method for operating a peritoneal dialysis (PD) machine disposed on a cart is disclosed. The cart includes a power supply for the PD machine. The method includes the steps of: initiating a dialysis treatment cycle that includes at least one of a drain phase, a fill phase, or a dwell phase; receiving a signal from the cart via a wireless communications channel indicating the cart is in motion; responsive to receiving the signal indicating that the cart is in motion, pausing the dialysis treatment cycle; receiving a signal from the cart via the wireless communications channel indicating the cart is stationary; and responsive to receiving the signal indicating that the cart is stationary, resuming the dialysis treatment cycle. In an embodiment, pausing the dialysis treatment cycle comprises at least one of: clamping at least one line connected to the PD machine; or moving at least one pump to a home position.

In some embodiments, the method also includes the step of charging one or more energy storage devices included in the cart when the cart is proximate a docking station. The docking station is configured to provide power to a charging circuit of the power supply via inductive charging.

In some embodiments, the method also includes, while the cart is in motion, detecting an object in a path of the cart, and engaging an automatic braking system of the cart responsive to detecting the object.

DETAILED DESCRIPTION

Figure 1:
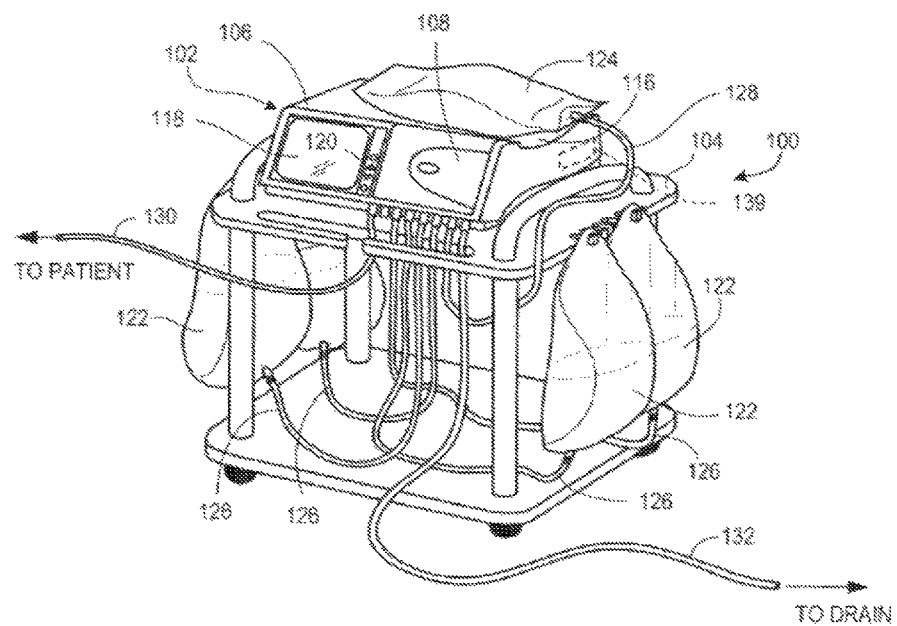
FIG. 1 illustrates a peritoneal dialysis (PD) system, in accordance with the prior art.

A mobile cart for a medical device, such as a PD machine, is described below. The cart can include a power supply for the medical device that allows a patient to be mobile during treatment, moving the medical device from location to location without having a wired connection to a fixed electrical supply such as a wall outlet. The power supply can include one or more batteries as well as a charging system. In some embodiments, the cart is associated with a wireless charger included in a docking station that, when the cart is in proximity to the docking station, can wirelessly charge the batteries via inductive charging.

When the cart is combined with a PD machine for dialysis treatment, the PD machine can be plugged into an outlet incorporated into the cart, where the outlet is connected to the power supply of the cart. In this manner, the patient does not need to unplug the PD machine from the wall outlet to move the PD machine. In some cases, the power supply of the cart includes an inverter to convert a DC (direct current) voltage supplied by the batteries into an AC (alternating current) voltage (e.g., 120/220 VAC) similar to that provided by a standard wall outlet. In other embodiments, the PD machine can be designed to be connected to a DC power source, either as the lone power supply or as an alternative power supply to the standard AC power supply (e.g., using a second cable).

The cart can also include a number of additional features including a wireless communication module to communicate with a wireless access point (AP) such as an AP provided by a wireless router that implements at least one IEEE 802.11 WiFi standard. In some embodiments, the cart can be connected to the medical device through a wired communications interface, thereby adding a wireless capability to a legacy device that does not include wireless capabilities. In some embodiments, the wireless communication module enables the cart to provide a wireless AP for a wireless local area network (WLAN) so that one or more accessories and/or the medical device can connect to the WLAN to communicate via the cart (i.e., the cart can provide a wireless router capability). In other embodiments, the wireless communication module can communicate with the medical device via a wireless interface such as a near field communication (NFC) or Bluetooth wireless interface. The cart can include additional sensors that can provide information to the medical device via the wireless interface. For example, a charging system of the power supply can send information to the medical device indicating a charge state of the power supply such that the medical device can display an indication of the charge state of the batteries in the cart (e.g., on a display of the medical device, using LEDs included in the medical device, using a speaker of the medical device, etc.).

In some embodiments, the cart can include sensors for monitoring an environment around the cart. For example, the sensors can detect objects in the cart's path, or a GPS unit to provide information about the location of the cart. In other embodiments, the cart can include air quality sensors, temperature sensors, humidity sensors, smoke detectors, carbon monoxide detectors, or the like.

In some embodiments, the cart can include accessories of convenience to the patient, such as an inductive charging station for a cellular phone or other portable electronic device. The cart can include a light that illuminates the area around the cart (e.g., "white" LED lights), and the light can include a UV light source to sterilize the surface of the medical device after treatment. In some embodiments, the cart can include an extendable tray that provides a work surface for the patient adjacent to the medical device. The cart can also include a UV light that turns on for a period of time when the tray is stowed in order to sterilize the surface of the tray.

It will be appreciated that the cart is optimized for use with a PD machine for use in a patient's home or a clinic during dialysis treatment. However, other types of medical devices can be utilized with the cart in lieu of the PD machine.

FIG. 1 illustrates a peritoneal dialysis (PD) system 100, in accordance with the prior art. The PD system 100 can include a PD machine 102, which can alternately be referred to as a PD cycler, seated on a cart 104. The PD machine 102 includes a housing 106, a door 108, and a cassette interface 110 that contacts a disposable PD cassette 112 when the cassette 112 is disposed within a cassette compartment 114 formed between the cassette interface 110 and the closed door 108. The cassette compartment 114, cassette interface 110, and cassette 112 are shown in more detail in FIG. 2. A heater tray 116 is positioned on top of the housing 106. The heater tray 116 is sized and shaped to accommodate a bag of PD solution such as dialysate (e.g., a 5 liter bag of dialysate). The PD machine 102 also includes a user interface such as a touch screen display 118 and additional control buttons 120 that can be operated by a user (e.g., a caregiver or a patient) to allow, for example, set up, initiation, and/or termination of a PD treatment.

Dialysate bags 122 are suspended from fingers on the sides of the cart 104, and a heater bag 124 is positioned in the heater tray 116. The dialysate bags 122 and the heater bags 124 are connected to the cassette 112 via dialysate bag lines 126 and a heater bag line 128, respectively. The dialysate bag lines 126 can be used to pass dialysate from dialysate bags 122 to the cassette 112 during use, and the heater bag line 128 can be used to pass dialysate back and forth between the cassette 112 and the heater bag 124 during use. In addition, a patient line 130 and a drain line 132 are connected to the cassette 112. The patient line 130 can be connected to a patient's abdomen via a catheter and can be used to pass dialysate back and forth between the cassette 112 and the patient's peritoneal cavity during use. The catheter may be surgically implanted in the patient and connected to the patient line 130 via a port, such as a fitting, prior to the PD treatment. The drain line 132 can be connected to a drain or drain receptacle and can be used to pass dialysate from the cassette 112 to the drain or drain receptacle during use.

The PD machine 102 also includes a control unit 139 (e.g., a processor, controller, system-on-chip (SoC), or the like). The control unit 139 can receive signals from and transmit signals to the touch screen display 118, the control panel 120, and the various other components of the PD system 100. The control unit 139 can control the operating parameters of the PD machine 102. In some embodiments, the control unit 139 includes an MPC823 PowerPC device manufactured by Motorola, Inc. As further discussed in detail elsewhere herein, in some embodiments, the control unit 139 may be configured to control disengaging and/or bypassing of a pump in connection with naturally draining the dialysate from a patient during the drain phase of a PD cycle.

Figure 2:
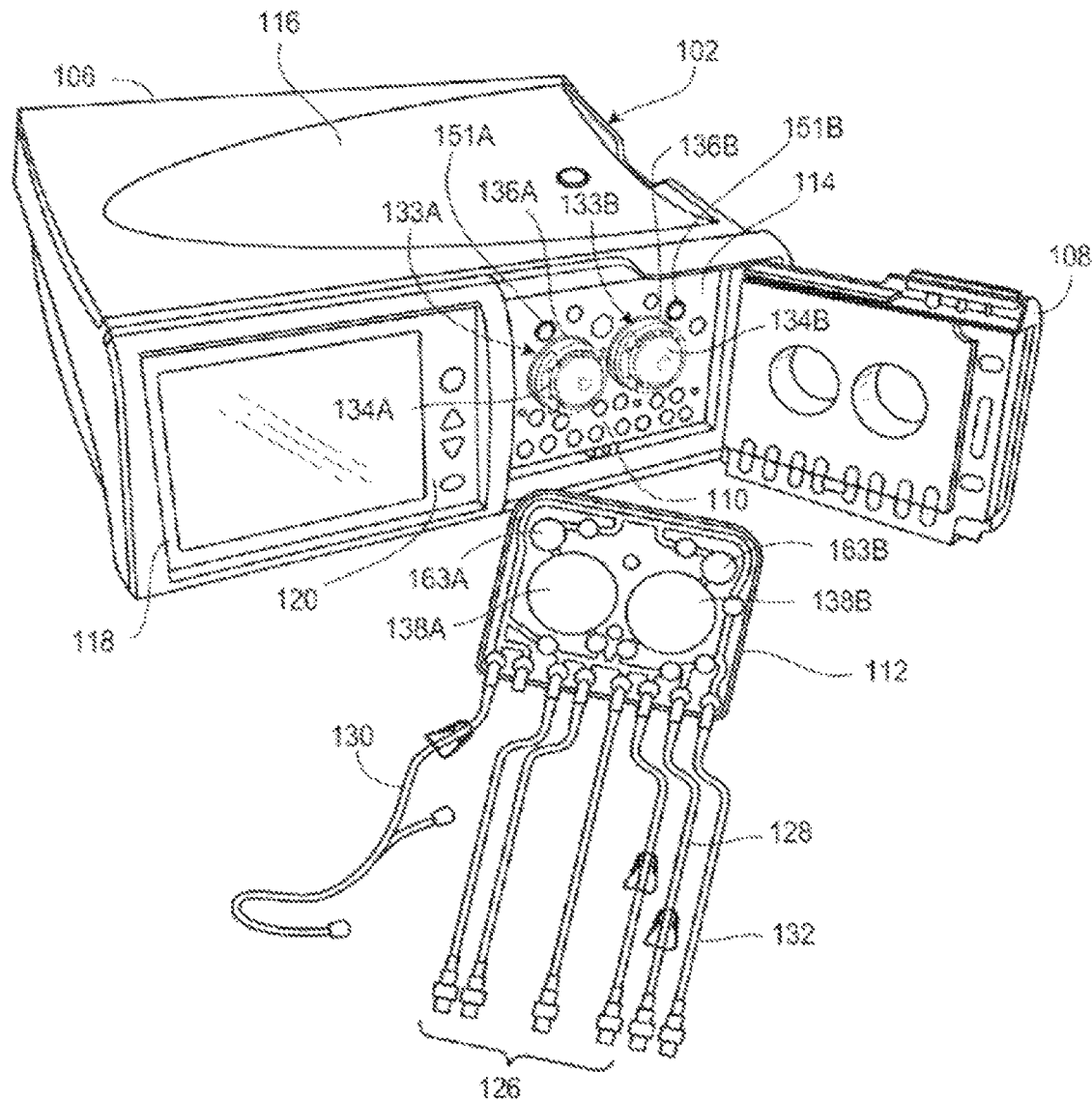
FIG. 2 is a perspective view of the PD machine and the PD cassette of the PD system of FIG. 1, in accordance with the prior art.

FIG. 2 is a perspective view of the PD machine 102 and the PD cassette 112 of the PD system 100 of FIG. 1, in accordance with the prior art. As depicted in FIG. 2, the PD cassette 112 is placed proximate the cassette interface 110. The cassette 112 contains pump chambers 138A, 138B, pressure sensing chambers 163A, 163B, and valve chambers for controlling the flow of fluid through the cavities of the cassette 112. The cassette 112 is connected to the dialysate bag lines 126, the heater bag line 128, the patient line 130, and the drain line 132.

The cassette interface 110 includes a surface having holes formed therein. The PD machine 102 includes pistons 133A, 133B with piston heads 134A, 134B attached to piston shafts. The piston shafts can be actuated to move the piston heads 133A, 133B axially within piston access ports 136A, 136B formed in the cassette interface 110. The pistons 133A, 133B are sometimes referred to herein as pumps. In some embodiments, the piston shafts can be connected to stepper motors that can be operated to move the pistons 133A, 133B axially inward and outward such that the piston heads 134A, 134B move axially inward and outward within the piston access ports 136A, 136B. The stepper motors drive lead screws, which move nuts inward and outward on the lead screws. The stepper motors can be controlled by driver modules. The nuts, in turn, are connected to the piston shafts, which cause the piston heads 134A, 134B to move axially inward and outward as the stepper motors drive the lead screws. Stepper motor controllers provide the necessary current to be driven through the windings of the stepper motors to move the pistons 133A, 133B. The polarity of the current determines whether the pistons 133A, 133B are advanced or retracted. In some embodiments, the stepper motors require 200 steps to make a full rotation, and this corresponds to 0.048 inches of linear travel of the piston heads 134A, 134B.

In some embodiments, the PD system 100 also includes encoders (e.g., optical quadrature encoders) that measure the rotational movement and direction of the lead screws. The axial positions of the pistons 133A, 133B can be determined based on the rotational movement of the lead screws, as indicated by feedback signals from the encoders. Thus, measurements of the position calculated based on the feedback signals can be used to track the position of the piston heads 134A, 134B of the pistons 133A, 133B.

When the cassette 112 is positioned within the cassette compartment 114 of the PD machine 102 with the door 108 closed, the piston heads 134A, 134B of the PD machine 102 align with the pump chambers 138A, 138B of the cassette 112 such that the piston heads 134A, 134B can be mechanically connected to dome-shaped fastening members of the cassette 112 overlying the pump chambers 138A, 138B. As a result of this arrangement, movement of the piston heads 134A, 134B toward the cassette 112 during treatment can decrease the volume of the pump chambers 138A, 138B and force dialysate out of the pump chambers 138A, 138B. Retraction of the piston heads 134A, 134B away from the cassette 112 can increase the volume of the pump chambers 138A, 138B and cause dialysate to be drawn into the pump chambers 138A, 138B.

The cassette 112 also includes pressure sensor chambers 163A, 163B. When the cassette 112 is positioned within the cassette compartment 114 of the PD machine 102 with the door 108 closed, pressure sensors 151A, 151B align with the pressure sensor chambers 163A, 163B. Portions of a membrane that overlies the pressure sensor chambers 163A, 163B adhere to the pressure sensors 151A, 151B using vacuum pressure. Specifically, clearance around the pressure sensors 151A, 151B communicates vacuum to the portions of the cassette membrane overlying the pressure sensing chambers 163A, 163B to hold those portions of the cassette membrane tightly against the pressure sensors 151A, 151B. The pressure of fluid within the pressure sensing chambers 163A, 163B causes the portions of the cassette membrane overlying the pressure sensor chambers 163A, 163B to contact and apply a force to the pressure sensors 151A, 151B.

The pressure sensors 151A, 151B can be any sensors that are capable of measuring the fluid pressure in the pressure sensor chambers 163A, 163B. In some embodiments, the pressure sensors are solid state silicon diaphragm infusion pump force/pressure transducers. One example of such a sensor is the model 1865 force/pressure transducer manufactured by Sensym® Foxboro ICT. In some embodiments, the force/pressure transducer is modified to provide increased voltage output. The force/pressure transducer can, for example, be modified to produce an output signal of 0 to 5 volts.

Figure 3:
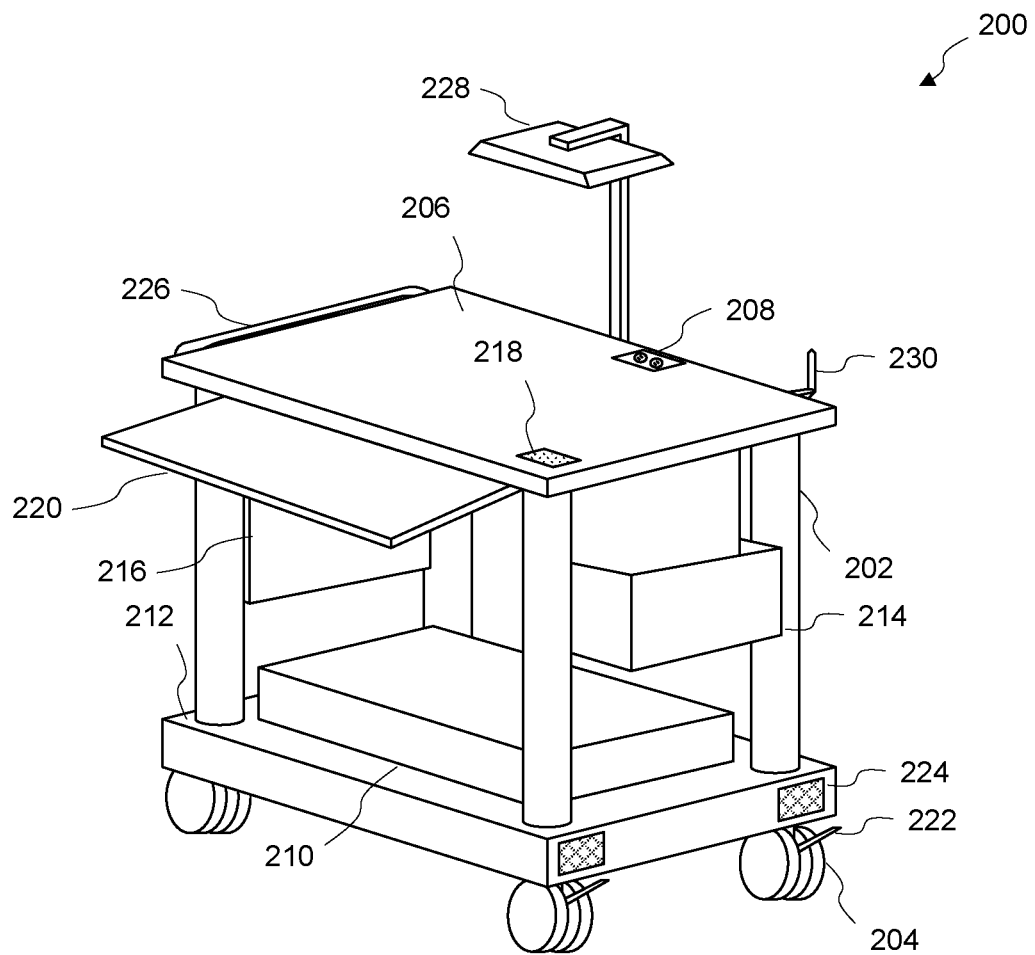
FIG. 3 is an illustration of a cart, in accordance with some embodiments.

FIG. 3 is an illustration of a cart 200, in accordance with some embodiments. The cart 200 can replace the cart 104 of the PD system 100. As depicted in FIG. 2, the cart 200 includes a structure 202 (e.g., legs, panels, connectors, etc.) mounted on four casters 204 (e.g., wheels) that allow the cart 200 to roll across a floor. A top surface 206 of the cart 200 provides sufficient surface area to place a medical device such as the PD machine 102. An electrical outlet 208 is located on the top surface 206 of the cart and provides a location for connecting a plug attached to the medical device to a power supply 210 located on a bottom surface 212 of the cart 200.

In some embodiments, the power supply 210 includes all energy storage devices as well as associated electronics for providing power to the medical device or other accessories of the cart 200. In an embodiment, the power supply 210 includes one or more energy storage devices (e.g., batteries, capacitors, fuel cells, etc.), an inverter, and a charging circuit. The energy storage devices are sized to provide the medical device with power for a desired length of time without connecting the cart 200 to an external power supply, such as a wall outlet. In an embodiment, batteries included in the cart 200 produce DC power (e.g., 12 VDC, 24 VDC, etc.), which can be routed to various components incorporated into the cart 200 that may require DC power (e.g., sensors, lights, etc.). Alternatively, an inverter can convert the DC power to an AC power (e.g., 120 VAC, 220 VAC, etc.) to run various equipment that may require AC power.

In an embodiment, the charging circuit allows the cart to be plugged into a wall outlet to recharge the batteries and/or supply external power to the electrical outlet 208 (i.e., when the cart is immobile). This allows the cart 200 to be fully charged between treatments or enables the cart 200 to run the medical device off the external supply when the patient wishes to do so. The cart can then be unplugged to continue treatment in a new location using the internal power supply 210.

In other embodiments, the charging circuit includes a coil suitable for use with an inductive charger. In such embodiments, the cart 200 does not need to be directly connected to an external power supply to re-charge the batteries. Instead, the cart may be placed proximate an external coil that will induce a current in the coil attached to the charging circuit, which provides the electricity needed to re-charge the batteries. An example of an external charging station that utilizes inductive charging is described in more detail in FIG. 4.

In an embodiment, the cart 200 includes trays 214, 216 for storing medical supplies such as dialysate bags and/or drain bags. The trays 214, 216 can be hung on the front or back of the cart 200 (or sides). In some embodiments, the trays 214, 216 are waterproof to protect any leaking liquid from affecting the power supply 210 below. In an embodiment, the trays 214, 216 can include a liquid sensor to detect leaks. If a leak is detected, the cart 200 can notify the medical device, which pauses a treatment session and/or can inform the patient of the potential leak. In some embodiments, the edge of the top surface 206 can include fingers or other structures for hanging bags or other items from the edge or underside of the top surface 206. It will be appreciated that the trays 214, 216 are designed for use with a dialysis system, but alternative designs suitable for use with other types of medical devices are contemplated as being incorporated in addition to or in lieu of the trays.

Additional accessories are incorporated into the cart for the convenience of the patient. For example, a charging station 218 for a portable electronic device (e.g., cellular phone, tablet computer, etc.) can be incorporated into the top surface 206. The charging station 218 can include a wired charging port (e.g., a Universal Serial Bus—USB) or a wireless charging device such as an inductive charger. In some embodiments, the cart 200 includes an extendable tray 220 that can be used to place items such as a paper, tablet computer, or book while a patient is undergoing treatment or for use in handling dialysis treatment supplies and disposables before and after the treatment. The extendable tray 220 can be stowed under the top surface 206. In an embodiment, a UV (ultraviolet) light (not explicitly shown) is incorporated into the underside of the top surface 206 such that, when the extendable tray 220 is stowed, the UV light operates to sterilize the surface of the extendable tray 220.

In some embodiments, the cart 200 also includes manual brakes 222 on the casters 204 that allow a person to lock the wheels so that the cart does not roll around. The person would then release the brakes 222 in order to make the cart mobile. In some embodiments, the brakes 222 can be actuated automatically (e.g., using a solenoid) or manually. Automatic brake systems enable safety features to be incorporated into the cart.

In one embodiment, the cart 200 includes sensors 224 that can provide the cart with object detection capabilities. For example, radar, sonar, image sensors, or other types of sensors for detecting objects can be incorporated into the front of the cart 200 and used to detect objects in the path of the cart 200. When the user pushes the cart too close to an object, the cart 200 may automatically engage the brakes 222 on the casters 204 to avoid hitting the object. Similarly, the sensors 224 can be configured to detect hazards such as stairs (e.g., edge detection) and automatically engage the brakes 222 to prevent the user from accidentally pushing the cart 222 down a flight of stairs. This can be a useful safety feature as many patients will typically undergo treatment during the night, and the patient may be tired or the room may be dark when the patient goes to move the cart 200 to, e.g., use the restroom.

In an embodiment, object detection is performed using sensors 224 such as an array of optical sensors, light detection and ranging (LiDAR) sensors, radar that utilizes the 75-110 GHz radio portion of the electromagnetic spectrum, or ultrasound (e.g., approximately 48 kHz audio frequency) detectors that are positioned around the outside or bottom edge of the cart. These sensors 224 can be utilized to detect a change in distance to a surface in front of the cart. If the distance gets shorter, then this can indicate the potential presence of an object such as a chair or a step at the bottom of a stairway. If the distance gets longer, then this can indicate the potential presence of a drop off such as the first step at the top of a stairway. In either case, the cart 200 may be configured to apply the braking mechanism to prevent the cart 200 from hitting an object in the path of the cart 200 or allowing the user to unwittingly push the cart 200 off a ledge.

In another embodiment, the cart 200 includes a handle 226 that allows a person to push the cart 200. The handle 226 can incorporate one or more sensors (e.g., mechanical switches, capacitive sensors, etc.) for detecting when a person is grasping the handle 226. When a person grasps the handle 222, the brakes 222 are automatically released. When the person lets go of the handle 222, the brakes 222 are automatically engaged. In some embodiments, the brakes 222 are released upon activation (e.g., detecting the handle being grasped) of the handle 226. However, the brakes 222 are engaged only after the cart 200 remains motionless for a threshold period of time.

The cart 200 may also include a light 228 that illuminates the top surface 206 and/or an immediately vicinity around the cart 200. In some embodiments, the light 228 is adjustable (e.g., height, orientation) and can provide white light (or any other color) for the user to easily see the medical device. For example, the light 228 can illuminate the user interface of the PD machine to make it easier for the patient or caregiver to adjust the PD treatment. The light 228 can also provide a reading light for the patient to read a book or magazine during treatment. In an embodiment, the light 228 can also include a UV light source to help sterilize the medical device or top surface 206 of the cart 200. In an embodiment, the light 228 is configured to turn on automatically when the cart 200 is not being charged. In other words, if the charging circuit is not receiving power from an external source, and the cart 200 is running off of the batteries, then the light may turn on as this could be an indication of a power failure (i.e., where the user may not have light in the room to easily see the medical device). In other embodiments, the cart is equipped with a microphone to detect when the PD machine 102 is setting off an alarm such that the noise (or other configurable audio wave) triggers the light to automatically turn on to illuminate the treatment area. In some cases, the microphone can respond to audio waves that enable the user to turn on the light via voice command.

Although not shown explicitly, the cart 200 can include various electronic components such as a microcontroller, processor (e.g., CPU), digital signal processor (DSP), or the like for controlling various functions of the cart 200. The cart 200 can also include memory (e.g., random access memory, flash memory, solid state drive, etc.) for storing programs and/or instructions executed by the processor(s)/controller(s). In an embodiment, the cart 200 includes a communications module for communicating with the medical device such as the PD machine 102 or a client device (e.g., a mobile phone). The communications module can include a network interface controller (NIC), modem, transceiver, one or more antennas, or the like.

As shown in FIG. 3, the cart 200 includes a wireless antenna 230 and/or a WiFi signal booster, and the cart 200 can be configured to communicate with an access point (AP) within range of the cart 200. The cart 200 can be configured to join a wireless network (e.g., WLAN) to communicate with the medical device, a client device such as a mobile phone or a tablet computer, or a server accessible through the local wireless network over a wide area network such as the Internet. In some embodiments, the cart 200 can extend a wireless capability to legacy medical equipment that does not include such capabilities, allowing the medical equipment to be updated remotely.

In other embodiments, the cart 200 can include a near field communication (NFC) or Bluetooth capability that enables the cart 200 to communicate with medical device placed on the cart 200. Thus, information from sensors or other electronic components can be transmitted from the cart 200 to the medical device. The information can be utilized to change the operation of the medical device or the medical device can display the information to allow a user to view the information (e.g., a display device of the PD machine can display a battery life indicator that shows a state of charge of the power supply 210). In some embodiments, the cart 200 can include a speaker that allows the cart to beep or otherwise notify the patient that a remaining power of the power supply 210 is critical and inform the patient that the cart 200 should be connected to an external power source to re-charge the batteries.

Although not shown explicitly, the cart 200 can include a display or other indicator that can provide information to a patient or caregiver. For example, a battery indicator comprising a number of LEDs or a basic liquid crystal display could be included in the cart 200 to indicate a state of charge of the batteries. In another embodiment, a display such as a small LED or OLED display could be incorporated into the cart. In an embodiment, the display can include a touch-sensitive interface that allows the patient to manage various accessories attached to the cart 200.

In some embodiments, the cart 200 may include a dock for charging personal electronic items such as a cellular phone or a tablet computer using the power supply 210.

Alternatively, the cart 200 can include additional power outlets or USB ports for charging external devices.

In some embodiments, the cart 200 can be designed to hold multiple medical devices so that more than one patient can be treated simultaneously from the same cart 200. For example, a size of the cart 200 could be increased to hold two PD machines 102, which may make the cart 200 more suitable for use in a dialysis clinic.

In some embodiments, the cart 200 includes an auxiliary device such as a peritonitis sensor that can be coupled to a drain line of the disposable cassette 112 of the PD machine 102 in order to monitor the effluent drained from the patient to detect whether the patient may be suffering from peritonitis.

In some embodiments, the cart 200 can include a tablet computer including a display device that allows the patient to be monitored remotely or participate in telehealth video conference calls with a health professional (e.g., doctor, nurse, clinician, pharmacist, etc.). In some embodiments, the display device can allow the patient to watch tutorials or other videos that show the patient to learn how to use the medical device placed on the cart 200. The display device and/or tablet computer can also be connected to a remote network to allow the patient to access network-related resources directly from the cart 200.

In some embodiments, the cart 200 can include radio components that allow the cart to connect to a cellular network. The cart 200 can then communicate with a remote server through the cellular network, which may be helpful in locations that lack wide access to WiFi APs. The radio components could also connect to a broadband communication network via satellite(s) to access the Internet.

In some embodiments, the cart 200 could even be fitted with a solar panel (e.g., photovoltaic cell(s)) to assist in charging the power supply 210 when electrical service may be intermittent or of poor quality. Solar panels would also potentially allow for continued charging and treatment during national emergencies like hurricanes where public utilities may be unavailable for longer periods. Typically, patients may need to rely on generator backups that run on gasoline or diesel, but during certain emergencies fuel may be hard to get and/or the generators could break down, and having solar panels as an alternative could allow the continued treatment of the patient while the power situation is resolved.

Figure 4:
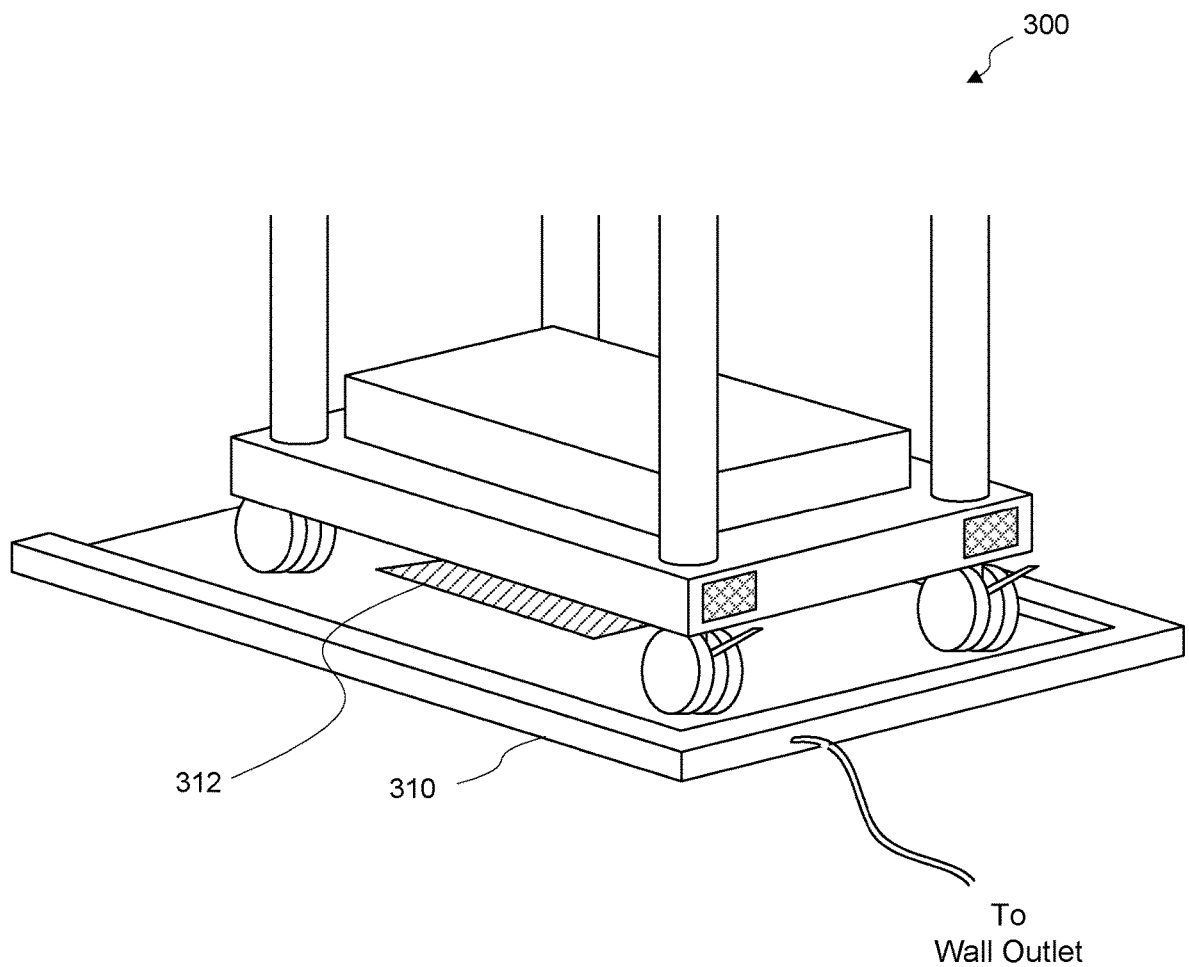
FIG. 4 illustrates a wireless charging system for the cart, in accordance with some embodiments.

FIG. 4 illustrates a wireless charging system 300 for the cart 200, in accordance with some embodiments. The wireless charging system 300 includes a docking station 310. The docking station provides a reference for a position of the cart 200 that will align the charging circuit of the power supply 210 with a charging circuit of the docking station 310. In an embodiment, a primary coil 312 in the docking station is connected to an external power supply such as a wall outlet. The primary coil is connected to an AC power source. In some embodiments, a switch activates the primary coil 312, allowing current to pass through the primary coil 312, when the cart 200 is inserted into the docking station 310. The switch can be mechanical (e.g., a contact is closed when the cart 200 rolls onto the surface of the docking station 310) or electrical (e.g., a light beam is broken or proximity sensor tripped when the cart 200 is rolled onto the docking station 310).

The electromagnetic field generated by the primary coil 312 induces a current in a secondary coil in the power supply 210 of the cart 200, which is used to re-charge the batteries and/or directly supply an AC current to the medical device. The secondary coil can be included in the charging circuit of the power supply 210. The AC current can be passed through a rectifier to generate a DC current for charging the batteries.

In some cases, a patient may place multiple docking stations 310 at different locations throughout their home, allowing the patient to move the cart 200 to any of the multiple docking stations 310 to re-charge the batteries of the cart 200.

Although the docking station 310 is shown as being larger than the footprint of the cart 200, in some embodiments, the docking station 310 is smaller than the cart's 200 footprint and, therefore, is located under the cart 200 between the casters 204 when the cart is in position. The docking station 310 may fit between the casters 204 such that the user rolls the cart 200 over the docking station 310 without rolling the cart 200 onto the docking station 310. A switch, such as a Hall effect sensor or image sensor, may still be configured to sense the presence of the cart 200 in order to activate the primary coil 312. In yet other embodiments, the docking station 310 may be positioned vertically against a wall and the secondary coil in the power supply 210 of the cart 200 may also be oriented vertically. Thus, the cart is simply rolled next to the vertical docking station 310 to initiate charging.

Figure 5:
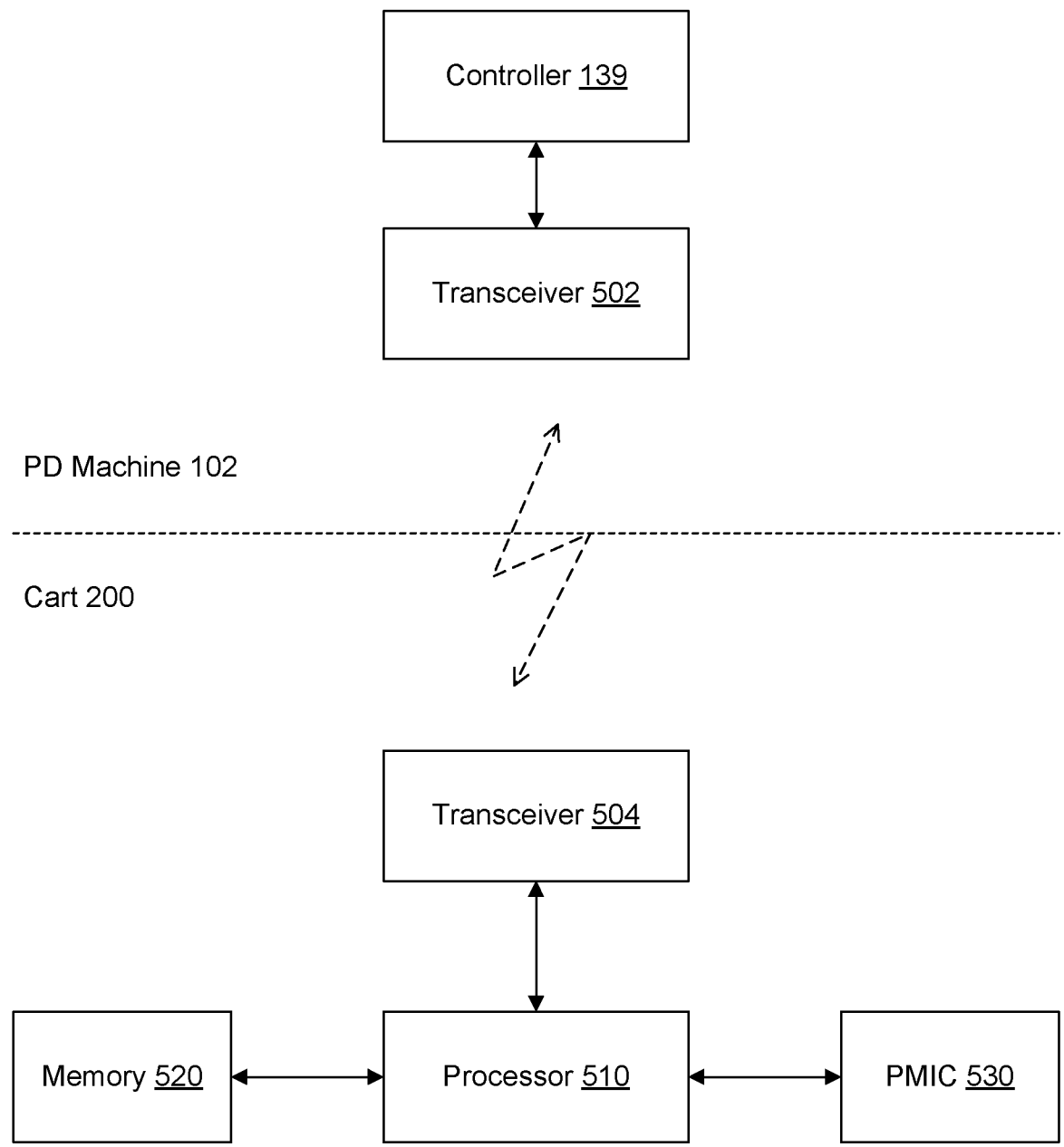
FIG. 5 illustrates a wireless communication channel for initiating communications between the cart and a medical device such as the PD machine, in accordance with some embodiments.

FIG. 5 illustrates a wireless communication channel for initiating communications between the cart 200 and a medical device such as the PD machine 102, in accordance with some embodiments. The PD machine 102 can be designed to include a transceiver 502 coupled to the controller 139. The transceiver 502 is attached to one or more antennas and enables the PD machine 102 to send and receive radio frequency (RF) signals through a wireless medium.

The cart 200 also includes a transceiver 504 that is connected to a processor 510. The transceiver 504 is also connected to one or more antennas and enables the cart 200 to send and receive RF signals through the wireless medium. The processor 510 can be, e.g., a microcontroller, a central processing unit (CPU), a DSP, an application specific integrated circuit (ASIC), and the like. The processor 510 can be connected to a memory 520 and a power management integrated circuit (PMIC) 530. The memory 520 stores data and instructions that can be executed by the processor 510. Although not shown explicitly, the processor 510 can also be connected to an input/output module to interface with external components such as sensors or user interface elements (such as an LED display or push buttons).

The PMIC 530 allows the processor to interface with the charging circuit of the power supply 210 to control charging or discharging of the batteries and supply of electricity to the various electrical components of the cart 200. The PMIC 530 can also control operation of a low voltage power supply that converts a voltage from the batteries (e.g., 24 VDC) to a low voltage suitable for the processor and other electrical components (e.g., 3.3 VDC, 5 VDC, etc.).

In an embodiment, the cart 200 is configured to function like an AP for a wireless local area network (WLAN). The cart 200 broadcasts a unique SSID and other peripheral devices can connect to the network using the SSID. Thus, even without access to a local WLAN provided by a home gateway or wireless router, the cart 200 can supply the necessary wireless network to let a variety of devices be interconnected wirelessly.

In another embodiment, the cart 200 is a client device that connects wirelessly to a separate WLAN as provided, for example, by a local wireless router or gateway. Once the devices are connected to the WLAN, the devices can communicate with each other using a local Internet Protocol (IP) address assigned to each device by the wireless router or gateway.

In yet other embodiments, the cart 200 functions as a near field communication (NFC) device and or a Bluetooth device. In such cases, the cart 200 can discover other devices within range that implement the same standards and connect to those devices directly.

It will be appreciated that, in some cases, the processor 510 is connected to a separate and distinct network interface controller (NIC), which is in turn connected to the transceiver 504. Any number or arrangement of components for implementing wireless communication is contemplated as being within the scope of the present disclosure.

Figure 6:
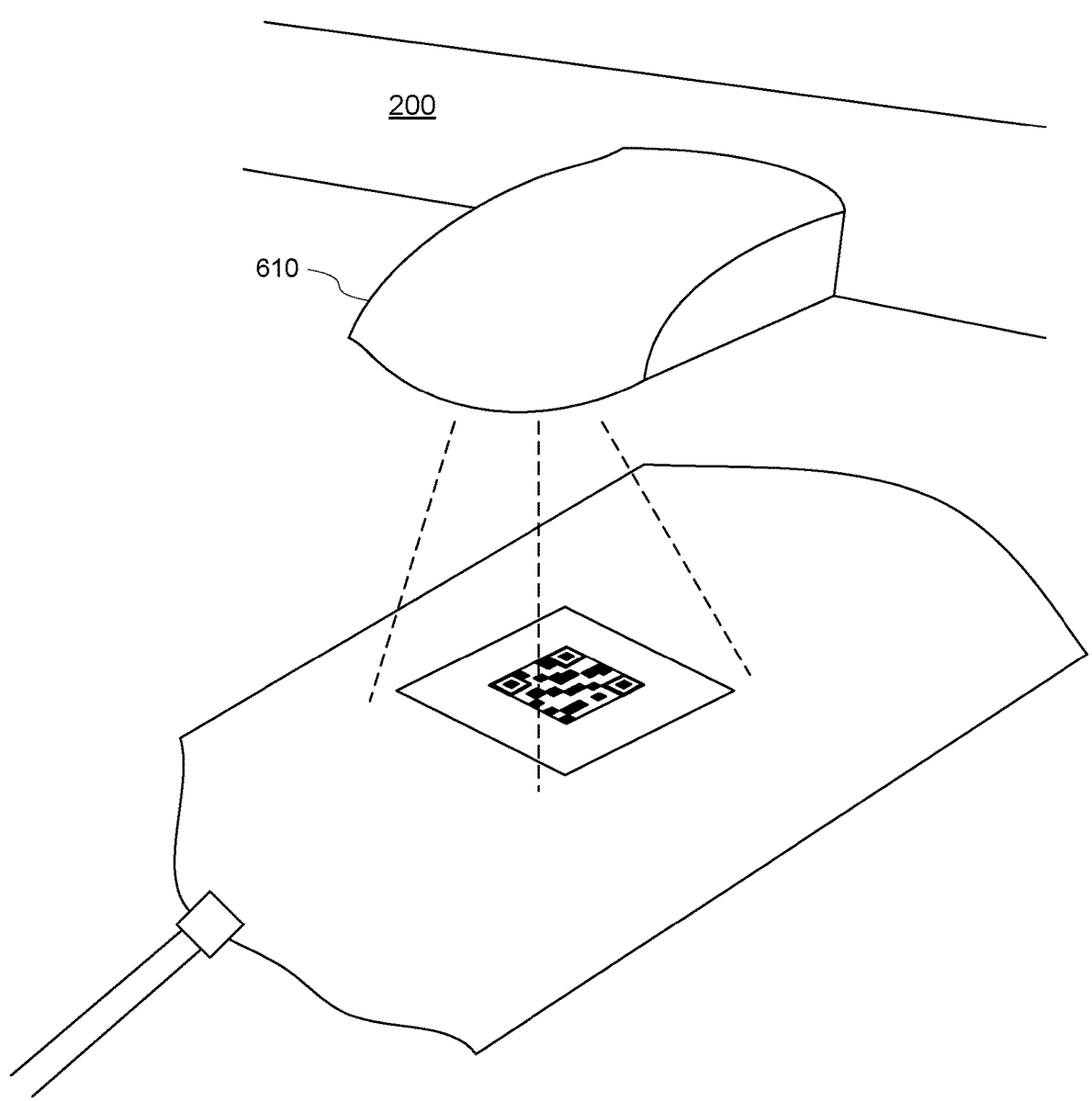
FIG. 6 illustrates a scanning device, in accordance with some embodiments.

FIG. 6 illustrates a scanning device, in accordance with some embodiments. As depicted in FIG. 6, the cart 200 can include a scanning device 610 such as a bar code reader or QR code reader. The scanning device 610 can be used to scan labels on supplies used for treatment in order to read information off the labels automatically and transmit the information to the medical device. For example, a patient can be prescribed different solutions of dialysate having different concentrations of sugars or minerals dissolved in the solution. The PD machine 102 can be configured to change an amount of fluid pumped into or drained from the patients abdomen depending on the concentration of the dialysate attached to the machine during a treatment. The prescription information can be uploaded to the PD machine 102 using a USB device or via the Internet, and the PD machine 102 can be configured to confirm that the bags being attached to the PD machine 102 match the prescription information based on the information read using the scanning device 610. If the information from the scanning device 610 does not match the prescription information, then the PD machine 102 can halt a treatment session and set an alarm to indicate that the patient or caregiver may have hooked up the wrong bag of dialysate to the PD machine 102.

Figure 7:
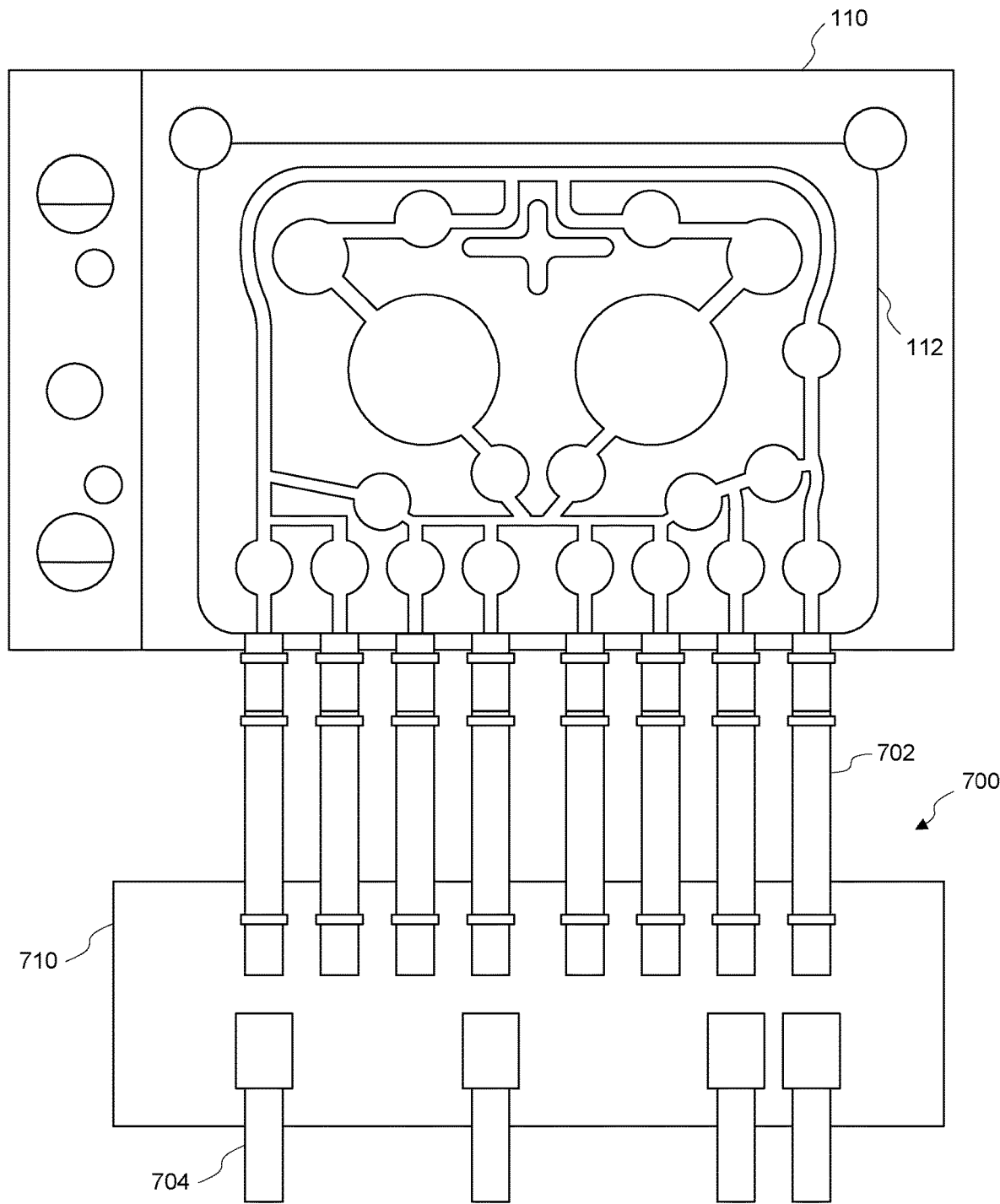
FIG. 7 illustrates a peritoneal dialysis assist device, in accordance with some embodiments.

FIG. 7 illustrates a peritoneal dialysis assist device 700, in accordance with some embodiments. When the cart 200 is being used with a PD machine 102, a patient may typically connect the various lines such as a tube connected to the catheter implanted in the patient to corresponding lines attached to a disposable cassette 112 inserted into the cassette interface 110 of the PD machine 102. With some patients, such as patients missing an arm or who suffer from other degenerative diseases such as Parkinson's, this procedure can be difficult and there are line management systems that attempt to make this operation easier for the patient. In addition, line management systems may reduce the risk of contamination as patients are not touching open orifices at the connection points.

In some embodiments, the cart 200 can include a line management system 710 integrated into the structure of the cart 200 that aids a patient in making these connections. For example, the tubing 702 attached to the disposable cassette 112 is inserted into the line management system 710 and one or more tubes 704 connected to dialysate bags, the patient's catheter, or a drain line are inserted into the other side of the line management system 710. The line management system 710 is closed and an external lever can be operated to mate the corresponding connectors to connect the tubing. By mating the connectors in a secure environment, there is less of a chance of contamination than if a person were to make the connection manually. For example, the lines can include caps that are automatically removed or replaced by the line management system 710 when connectors are mated or separated, respectively. In some embodiments, the line management system 700 can be operated electronically using the power supply 210 of the cart 200 such that either closing a door or latch or subsequently pressing a button causes electric motors to mate the corresponding connectors. Examples of existing peritoneal dialysis assistance devices implemented as stand-alone devices include Peripal's Peri-Safe® and Baxter's UV-Flash Compact®.

In some embodiments, the peritoneal assist device is simply a structure molded into the top surface 206 of the cart that will hold one connector so a user can mate that connector to a separate corresponding connector. This type of peritoneal assist device, while not automated, allows a patient to make a connection one-handed.

Figure 8:
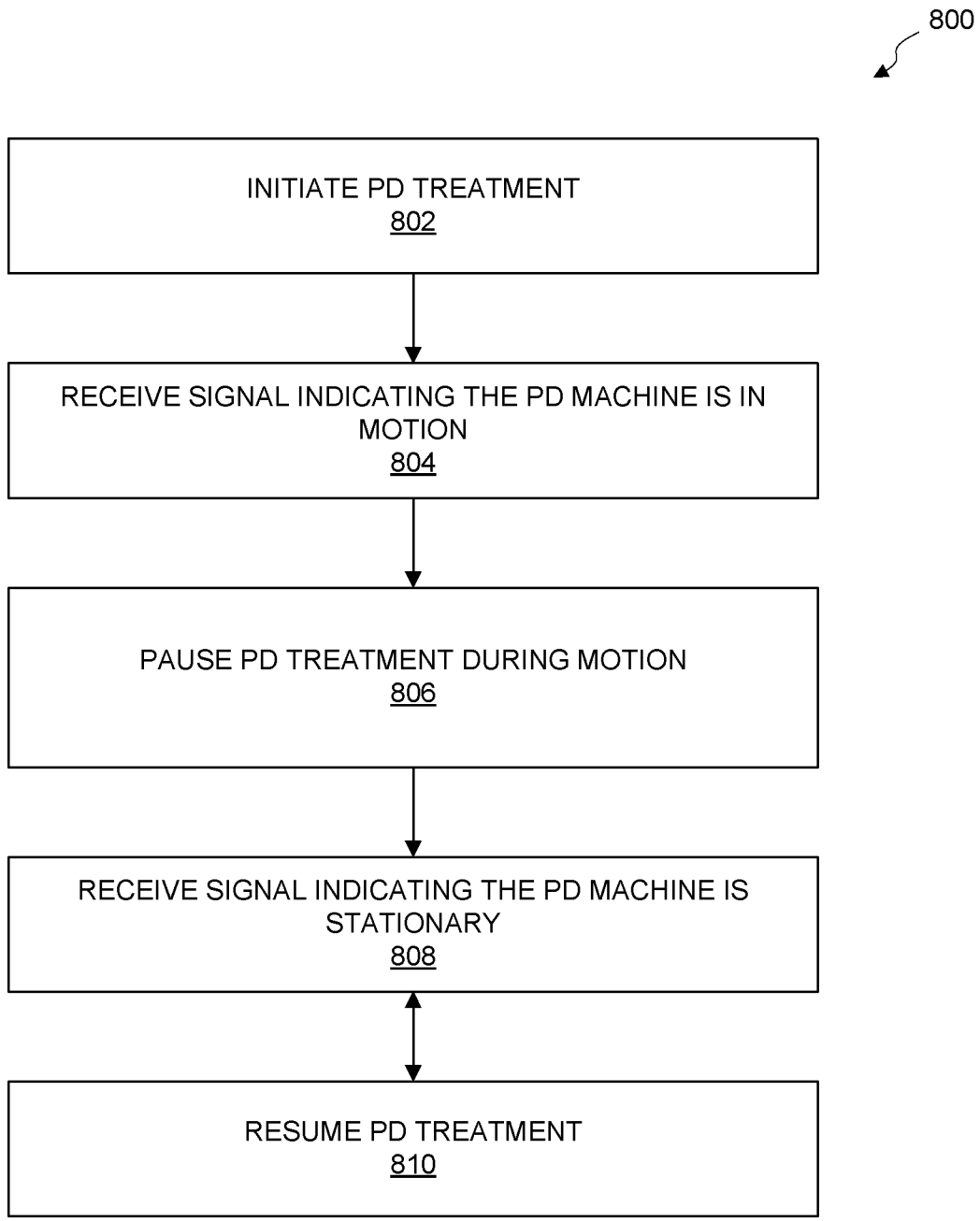
FIG. 8 is a flow diagram of a method for operating a dialysis machine, in accordance with some embodiments.

FIG. 8 is a flow diagram of a method 800 for operating a dialysis machine, in accordance with some embodiments. It will be appreciated that the method 800 is described as being performed by the PD machine 102. More specifically, the various steps described below can be implemented by a processor, such as the control unit 139 of the PD machine 102, configured to execute a number of instructions. In various embodiments, the method 800 can be implemented using hardware, software executed by a general purpose processor configured to control a specialized apparatus such as a PD machine, or a combination of hardware and software.

At step 802, a treatment session is initiated. In an embodiment, the PD machine 102 can start by initiating a drain phase of a PD treatment cycle. Dialysate is drained from the patient's abdomen that was left there during a previous PD treatment cycle. Once the effluent is drained, the PD machine 102 can switch to a fill phase of the PD treatment cycle, followed by a dwell phase of the PD treatment cycle. Alternatively, the PD treatment cycle can start with the fill phase, such as when the drain phase was the last phase in the previous PD treatment cycle.

At step 804, a signal indicating the PD machine is in motion is received. In an embodiment, the cart 200 includes sensors that monitor for movement of the cart 200. For example, the cart 200 can include accelerometers or other inertial measurement units that indicate when the cart is accelerating (i.e., moving). If the accelerometers detect motion above a threshold level, then the cart 200 can be configured to send a signal to the PD machine 102 that indicates the cart 200 and PD machine 102 are in motion.

At step 806, responsive to the signal indicating the PD machine is in motion, the treatment session is paused. In an embodiment, the PD machine 102 should not be operated while in motion as certain mechanism, such as pumps, may not be accurate when the pump is under acceleration. If motion is detected, then the PD treatment cycle is paused, such as by clamping certain fluid lines and moving the pumps or other components to a home position. No fluid is pumped into or out of the patient during this time.

At step 808, a signal indicating the PD machine is stationary is received. In an embodiment, the cart 200 is configured to monitor the sensors to detect a lack of motion. For example, if the signals from the accelerometers or other inertial measurement units remain below a threshold level for a minimum period of time, then the cart 200 transmits a signal to the PD machine 102 that indicates the cart 200 and the PD machine 102 are stationary.

At step 810, responsive to the signal indicating the PD machine is stationary, the treatment session is resumed. In an embodiment, the PD treatment session is resumed by unclamping one or more fluid lines and resuming operation of the pumps during a drain or fill phase of the PD treatment cycle.

Figure 9:
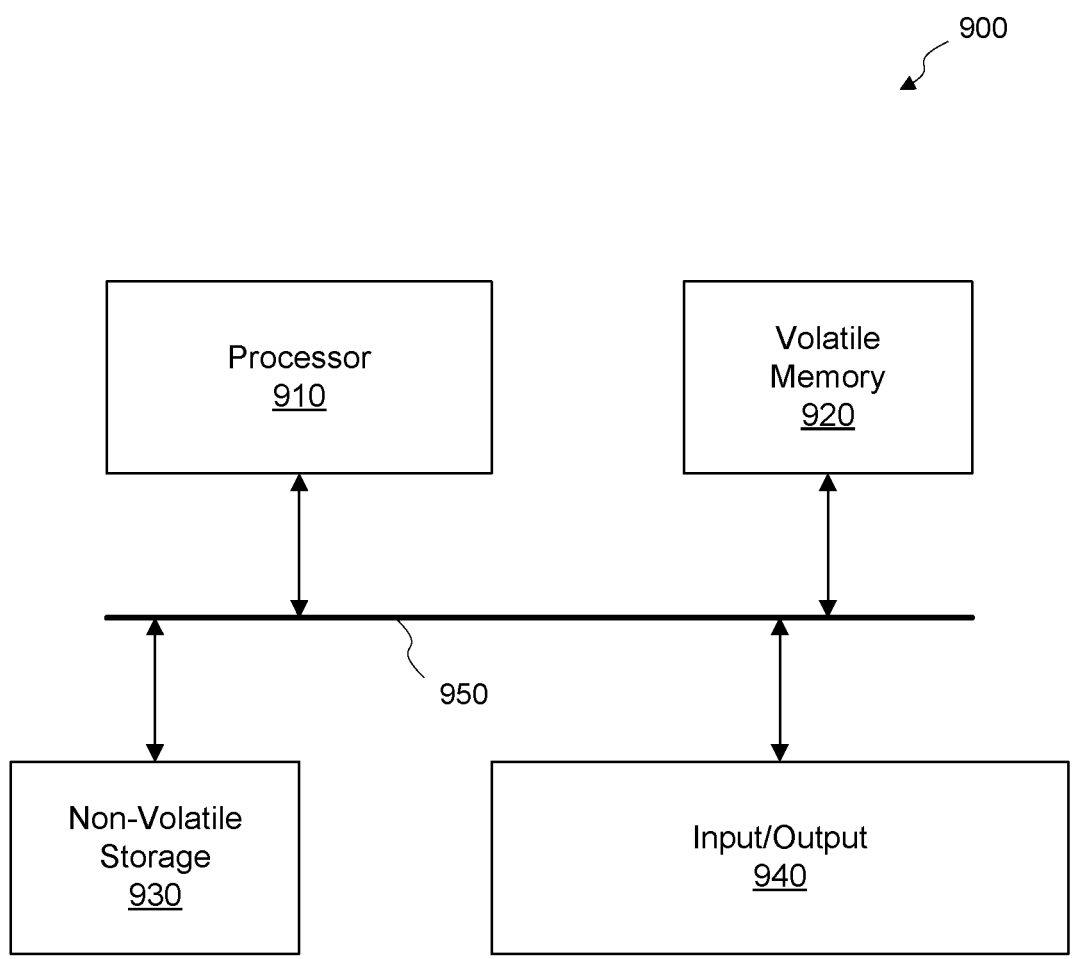
FIG. 9 illustrates an exemplary computer system, in accordance with some embodiments.

FIG. 9 illustrates an exemplary computer system 900, in accordance with some embodiments. It will be appreciated that, in various embodiments, the control unit 139 can be implemented, at least in part, to include the components of the computer system 900. In addition, the cart 200 can include one or more components of the computer system 900. The processor 910 can execute instructions that cause the computer system 900 to implement the functionality of the control unit 139 or cart 200, as described above.

As depicted in FIG. 9, the system 900 includes a processor 910, a volatile memory 920, a non-volatile storage 930, and one or more input/output (I/O) devices 940. Each of the components 910, 920, 930, and 940 can be interconnected, for example, using a system bus 950 to enable communications between the components. The processor 910 is capable of processing instructions for execution within the system 900. The processor 910 can be a single-threaded processor, a multi-threaded processor, a vector processor that implements a single-instruction, multiple data (SIMD) architecture, a quantum processor, or the like. The processor 910 is capable of processing instruction stored in the volatile memory 920. In some embodiments, the volatile memory 920 is a dynamic random access memory (DRAM). The instructions can be loaded into the volatile memory 920 from the non-volatile storage 930. In some embodiments, the non-volatile storage 930 can comprise a flash memory such as an EEPROM. In other embodiments, the non-volatile storage 930 can comprise a hard disk drive (HDD), solid state drive (SSD), or other types of non-volatile media. The processor 910 is configured to execute the instructions, which cause the PD machine 102 or cart 200 to carry out the various functionality described above.

In some embodiments, the memory 920 stores information for operation of the PD machine 102 or cart 200. For example, the operating parameters can be stored in the memory 920. The processor 910 can read the values of the operating parameters from the memory 920 and then adjust the operation of the PD machine 102 or cart 200 accordingly. For example, a speed of the pistons 133A, 133B can be stored in or written to the memory 920 and read from the memory 920. The speed is then used to control signals transmitted to the stepper motor drivers. As another example, network parameters for automatically connecting the cart 200 to a WLAN can be stored in the memory 920.

The I/O device(s) 940 provides input and/or output interfaces for the system 900. In some embodiments, the I/O device(s) 940 include a network interface controller (NIC) that enables the system 900 to communicate with other devices over a network, such as a local area network (LAN) or a wide area network (WAN) such as the Internet. In some embodiments, the non-volatile storage 930 can include both local and remote computer readable media. The remote computer readable media can refer to a network storage device such as a storage area network (SAN) or a cloud-based storage service. The I/O device(s) 940 can also include, but are not limited to, a serial communication device (e.g., RS-232 port, USB host, etc.), a wireless interface device (e.g., a transceiver conforming to WiFi or cellular communication protocols), a sensor interface controller, a video controller (e.g., a graphics card), or the like.

It will be appreciated that the system 900 is merely one exemplary computer architecture and that the control unit 139 or other processing devices can include various modifications such as additional components in lieu of or in addition to the components shown in FIG. 9. For example, in some embodiments, the control unit 139 can be implemented as a system-on-chip (SoC) that includes a primary integrated circuit die containing one or more CPU core, one or more GPU cores, a memory management unit, analog domain logic and the like coupled to a volatile memory such as one or more SDRAM integrated circuit dies stacked on top of the primary integrated circuit dies and connected via wire bonds, micro ball arrays, and the like in a single package (e.g., chip). The chip can be included in a chipset that includes additional chips providing the I/O device 940 functionality when connected to the SoC via a printed circuit board.

The system and techniques described herein are discussed for illustrative purposes principally in connection with a particular type of PD cycler, for example a PD cycler having piston-based pumps and a heater tray used to batch heat dialysate in a heater bag. It is noted that the system and techniques described herein may be suitably used in connection with other types and configurations of dialysis machines and/or medical devices involving the transmission of fluid to and from a patient via a patient line. For example, the system and techniques described herein may be used in connection with a PD cycler using a different configuration and style of pump, such as a peristaltic pump, and may be used in connection with other types of dialysate heating arrangements, such as in-line heating arrangements. Further, the system described herein may be suitably used in connection with other types of dialysis machines, including, for example, hemodialysis machines, and with other types of medical equipment that is unrelated to dialysis treatment.

It is noted that the techniques described herein may be embodied in executable instructions stored in a computer readable medium for use by or in connection with a processor-based instruction execution machine, system, apparatus, or device. It will be appreciated by those skilled in the art that, for some embodiments, various types of computer-readable media can be included for storing data. As used herein, a "computer-readable medium" includes one or more of any suitable media for storing the executable instructions of a computer program such that the instruction execution machine, system, apparatus, or device may read (or fetch) the instructions from the computer-readable medium and execute the instructions for carrying out the described embodiments. Suitable storage formats include one or more of an electronic, magnetic, optical, and electromagnetic format. A non-exhaustive list of conventional exemplary computer-readable medium includes: a portable computer diskette; a random-access memory (RAM); a read-only memory (ROM); an erasable programmable read only memory (EPROM); a flash memory device; and optical storage devices, including a portable compact disc (CD), a portable digital video disc (DVD), and the like.

It should be understood that the arrangement of components illustrated in the attached Figures are for illustrative purposes and that other arrangements are possible. For example, one or more of the elements described herein may be realized, in whole or in part, as an electronic hardware component. Other elements may be implemented in software, hardware, or a combination of software and hardware. Moreover, some or all of these other elements may be combined, some may be omitted altogether, and additional components may be added while still achieving the functionality described herein. Thus, the subject matter described herein may be embodied in many different variations, and all such variations are contemplated to be within the scope of the claims.

To facilitate an understanding of the subject matter described herein, many aspects are described in terms of sequences of actions. It will be recognized by those skilled in the art that the various actions may be performed by specialized circuits or circuitry, by program instructions being executed by one or more processors, or by a combination of both. The description herein of any sequence of actions is not intended to imply that the specific order described for performing that sequence must be followed. All methods described herein may be performed in any suitable order unless otherwise indicated herein or otherwise clearly contradicted by context.

The use of the terms "a" and "an" and "the" and similar references in the context of describing the subject matter (particularly in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. Furthermore, the foregoing description is for the purpose of illustration only, and not for the purpose of limitation, as the scope of protection sought is defined by the claims as set forth hereinafter together with any equivalents thereof. The use of any and all examples, or exemplary language (e.g., "such as") provided herein, is intended merely to better illustrate the subject matter and does not pose a limitation on the scope of the subject matter unless otherwise claimed. The use of the term "based on" and other like phrases indicating a condition for bringing about a result, both in the claims and in the written description, is not intended to foreclose any other conditions that bring about that result. No language in the specification should be construed as indicating any non-claimed element as essential to the practice of the invention as claimed.

What is claimed is:

1. A system for dialysis treatment, the system comprising:
a cart comprising one or more energy storage devices and a charging circuit;
a docking station connected to an electrical supply and configured to provide power to the charging circuit to recharge the one or more energy storage devices;
a dialysis machine disposed on the cart, wherein the dialysis machine is configured to be moved from location to location based on movement of the cart, and wherein the dialysis machine is configured to receive power from the one or more energy storage devices of the cart;
one or more dialysate bags disposed on the cart; and
a scanning device configured to scan one or more labels of the one or more dialysate bags;
wherein the cart further comprises:
an automatic braking system;
one or more sensors configured to detect an object in a path of the cart while the cart is in motion; and
a controller configured to engage the automatic braking system to stop the motion of the cart in response to detecting an object in the path of the cart;
wherein the controller of the cart is further configured to engage the automatic braking system to stop the motion of the cart in response to detecting a hazard, wherein detecting the hazard comprises performing edge detection to detect a ledge proximate to the cart; and
wherein the controller of the cart is further configured to:
determine whether information obtained via the scanning device matches prescription information for a patient; and
in response to the obtained information not matching the prescription information for the patient, stop a dialysis treatment being performed by the dialysis machine and/or generate an alarm.

2. The system of claim 1, wherein the docking station includes a primary coil, wherein the charging circuit of the cart includes a secondary coil, and wherein the primary coil is configured to induce a current in the secondary coil for charging the one or more energy storage devices of the cart.

3. The system of claim 2, wherein the docking station comprises a switch or sensor configured to activate the primary coil based on the cart being detected as proximate to the docking station.

4. The system of claim 1, wherein the cart further comprises one or more lights, wherein the one or more lights includes an ultraviolet (UV) light source for sterilizing at least one surface.

5. The system of claim 4, wherein the cart further comprises an extendable tray configured to be stowable under a top surface of the cart; and
wherein the UV light source is attached to an underside of the top surface for sterilizing at least part of the extendable tray while the extendable tray is in a stowed position.

6. The system of claim 1, wherein the cart comprises a line management system, wherein the line management system is configured to automatically remove and replace caps for fluid lines.

7. The system of claim 1, wherein the cart further comprises a wireless access point (AP).

8. The system of claim 1, wherein the cart further comprises a heater tray configured to accommodate a bag of dialysate.

9. The system of claim 1, wherein the cart further comprises a communications interface; and
wherein the controller is configured to obtain the prescription information of the patient via the communications interface.

10. A cart for providing a mobile dialysis treatment, the system comprising:
a surface configured for placement of a dialysis machine on the cart to move the dialysis machine from location to location based on movement of the cart;
one or more energy storage devices configured to provide power to the dialysis machine;
a charging circuit configured to receive power from a docking station and to recharge the one or more energy storage devices based on the received power;
one or more hooks for mounting one or more dialysate bags on the cart;
a scanning device configured to scan one or more labels of the one or more dialysate bags;
an automatic braking system;
one or more sensors configured to detect an object in a path of the cart while the cart is in motion; and
a controller configured to engage the automatic braking system to stop the motion of the cart in response to detecting an object in the path of the cart;
wherein the controller is further configured to engage the automatic braking system to stop the motion of the cart in response to detecting a hazard, wherein detecting the hazard comprises performing edge detection to detect a ledge proximate to the cart; and
wherein the controller is further configured to:

determine whether information obtained via the scanning device matches prescription information for a patient; and in response to the obtained information not matching the prescription information for the patient, stop a dialysis treatment being performed by the dialysis machine and/or generate an alarm.

11. The cart of claim 10, wherein the cart further comprises one or more lights, wherein the one or more lights includes an ultraviolet (UV) light source for sterilizing at least one surface.

12. The cart of claim 11, wherein the cart further comprises an extendable tray configured to be stowable under a top surface of the cart; and wherein the UV light source is attached to an underside of the top surface for sterilizing at least part of the extendable tray while the extendable tray is in a stowed position.

13. The cart of claim 10, wherein the cart comprises a line management system, wherein the line management system is configured to automatically remove and replace caps for fluid lines.

14. The cart of claim 10, wherein the cart further comprises a wireless access point (AP).

15. The cart of claim 10, wherein the cart further comprises a heater tray configured to accommodate a bag of dialysate.

16. The cart of claim 10, wherein the cart further comprises a communications interface; and wherein the controller is configured to obtain the prescription information of the patient via the communications interface.

* * * * *